United States Patent [19]

McLoughlin et al.

[11] 4,208,578
[45] Jun. 17, 1980

[54] OPTICAL INSPECTION APPARATUS

[75] Inventors: Robert W. McLoughlin; Colin P. Nuttall, both of Bangor, Northern Ireland

[73] Assignee: Gallaher Limited, Belfast, Northern Ireland

[21] Appl. No.: 870,447

[22] Filed: Jan. 18, 1978

[30] Foreign Application Priority Data

Nov. 28, 1977 [GB] United Kingdom ............... 49373/77

[51] Int. Cl.² ............................................. H01J 39/12
[52] U.S. Cl. .............................. 250/214 AG; 209/536
[58] Field of Search ............... 209/536; 250/223, 227, 250/214 AG, 214 A, 214 R, 562, 563, 572, 209; 356/200, 209

[56] References Cited
U.S. PATENT DOCUMENTS

| | | | |
|---|---|---|---|
| 3,729,636 | 4/1973 | Merker | 209/536 |
| 3,854,587 | 12/1974 | McLoughlin | 250/562 |
| 3,986,037 | 10/1976 | Faulhaber | 250/214 AG |

Primary Examiner—David C. Nelms
Attorney, Agent, or Firm—Andrus, Sceales, Starke & Sawall

[57] ABSTRACT

The invention relates to optical inspection apparatus for monitoring a continuously moving rod, the apparatus comprising a circular head through which the rod passes, a first set of fibre optic conductors which transmits light from a source to the head to illuminate the rod, and a second set of fibre optic conductors which pick up light reflected from the rod passing through the head and transmits the reflected light to a number of photoelectric elements. The second set of conductors are divided into angularly spaced groups around the head and adjacent groups lead to separate photoelectric elements. The outputs of the elements are fed via A.C. coupling means into separate channels connected to comparator means responsive to the noise signal level in the individual channels. The comparator means produces a fault pulse in the signal level in any one channel is greater than a preset allowable level. Each of the channels includes an amplifier for amplifying the noise signal, the level of the noise signal being fed back to control the amplifier gain so that the mean level of the amplified noise signal is maintained substantially constant.

9 Claims, 6 Drawing Figures

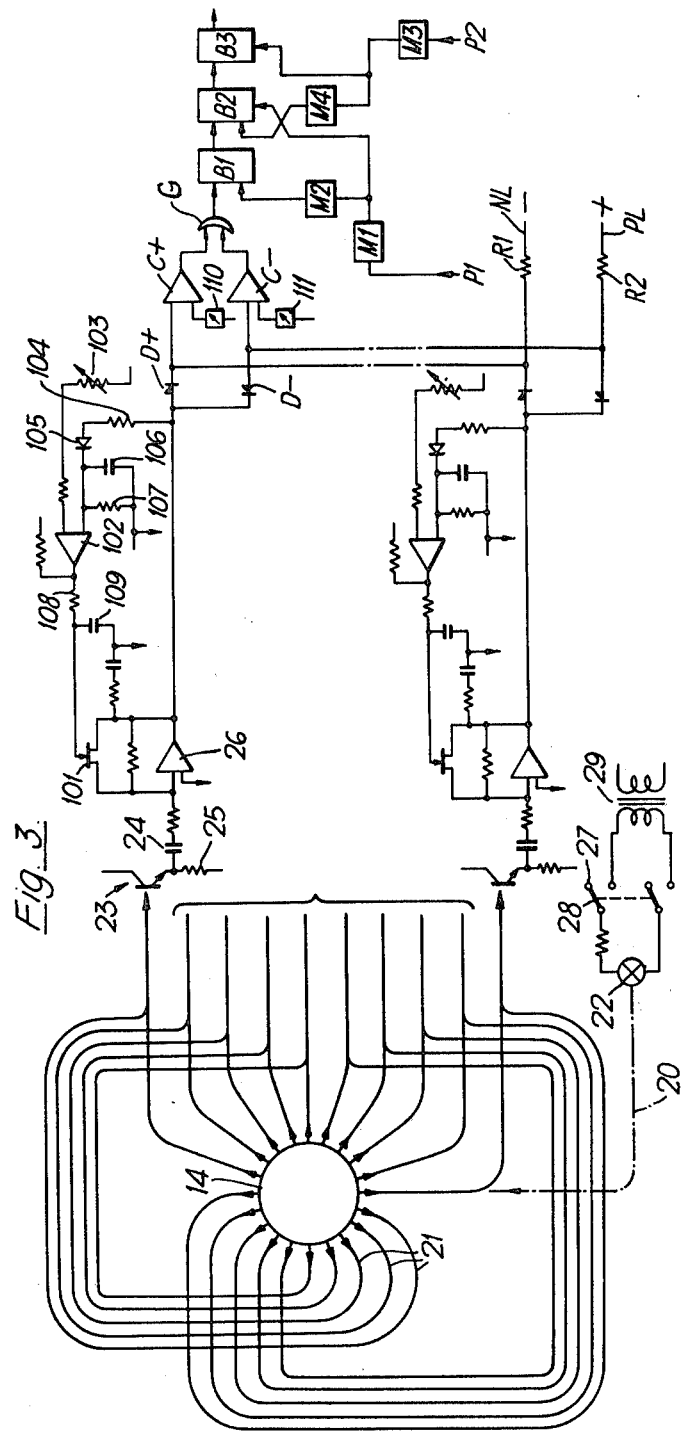

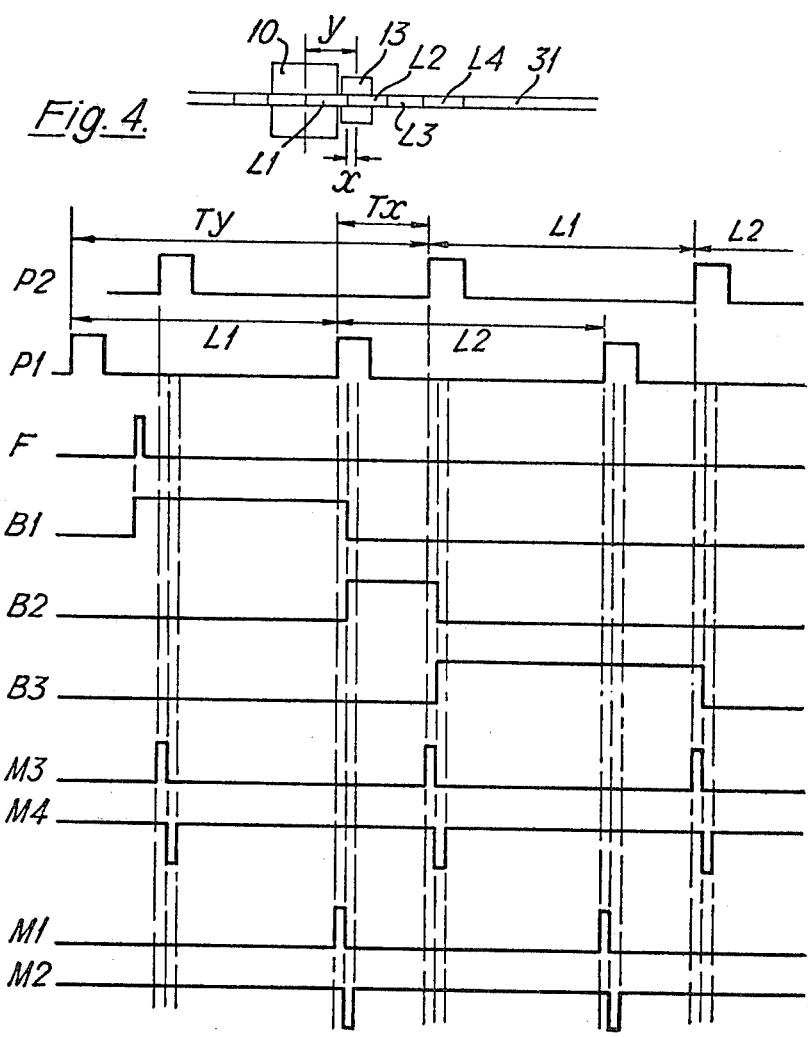
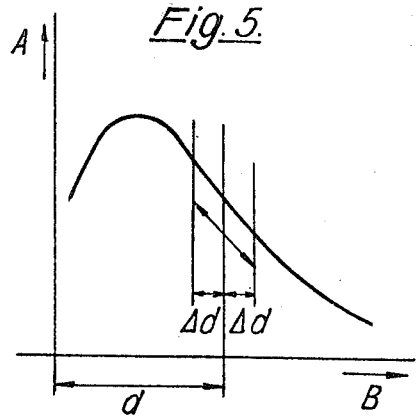
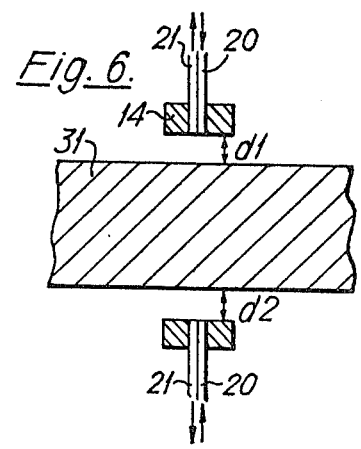

OPTICAL INSPECTION APPARATUS

BACKGROUND OF THE INVENTION

1. Field of the Invention

The invention is concerned with optical inspection apparatus for monitoring a continuously moving rod, for example a cigarette rod, and for sensing critical variations in the reflective properties of the rod's surface, corresponding to a flaw in the surface. In a tobacco rod such a flaw may be produced by an imperfect lap seal of the wrapper or a tear in the paper produced by a particularly hard piece of tobacco stem.

2. Description of the Prior Art

Conventionally, a cigarette inspection apparatus involves means for measuring the pressure drop caused by leaks in the surface of the cigarette assembly when air suction or pressure is applied. Methods have also been proposed, for example in British Patent Specification No. 1,135,183 or in U.S. Pat. No. 3,626,196, for inspecting a rod by illuminating the rod and detecting the reflected light on a number of photo electric cells. However none of these are entirely satisfactory for high speed production.

In our earlier U.S. Pat. No. 3,854,587, there is described an optical inspection device for monitoring a continuously moving rod and comprising a circular head through which the rod passes, a first set of fibre optic conductors the ends of which terminate at an inner peripheral surface of the head and which transmit light from a source to the head to illuminate the rod passing through the head, and a second set of fibre optic conductors the ends of which also terminate at an inner peripheral surface of the head to pick up light reflected from the rod passing through the head and transmit that light to a photo electric element, such as a photo transistor or photo diode, characterised in that the second set of fibre optic conductors are divided into angularly spaced groups round the head and adjacent groups lead to separate photo electric elements, the outputs of which are fed into separate channels connected to comparator means which is responsive to the signal level in the individual channels and which produces a fault signal if the signal level in any one channel is greater than a pre-set allowable level.

In the absence or rod faults, and as a result of AC coupling to the individual channels, the signal level in the individual channels consists of the AC noise produced by inevitable variation in the reflectivity of the rod as it passes through the inspection head. These variations are due, in the case of cigarette rod, to variation in the reflectivity of the paper wrapper, the variations in tobacco colour seen through the paper, and small variation in the distance of the paper wrapper from the ends of the second set of fibre optic conductors, caused by minor undulations in the rods surface. Faults such as holes, tears, open seams, and dirt spots cause a momentary fluctuation in reflected light which appears as a positive or negative pulse superimposed on the normal noise signal. The division of the second set of conductors into angularly spaced groups, leading to respective ones of the separate parallel channels, ensures that only a proportion of the area of rod surface is viewed by any one photo electric element so that any one channel only carries a noise signal corresponding to the acceptable fluctuations in a thin strip of the rod surface. This effectively increases the fault pulse/noise signal ratio in each channel and hence at the comparator means. The signal level, consisting of the noise signal plus any fault pulse, in each channel is compared with a reference or datum level in a comparator circuit corresponding to that channel, or, as described in the earlier specification, in a common comparator circuit to which the individual channels are connected by a maximum signal selector circuit arranged to transmit to the common comparator circuit the most positive and most negative signal levels existing at any time in any one of the channels.

Difficulties arise in maintaining and optimising the sensitivity and discrimination of the apparatus owing to variations in signal noise from the rod, a drift in the response characteristics of a component over a period of time resulting for example from dust deposit in the inspection head, and differential sensitivity of components related to the separate channels. All these factors can affect the amplitude of the noise signal and, as a result, the apparatus can overlook faults, when a fault pulse is not distinguishable from the noise signal, or incorrectly recognise the noise signal as a spurious fault pulse.

SUMMARY OF THE INVENTION

In accordance with the present invention, in an optical inspection apparatus of the kind described in our earlier Specification, each channel includes an amplifier for amplifying the electric output noise signal from a respective photo electric element, and means are provided for feeding back to each amplifier a signal related to the mean level of the amplified noise signal in that channel and thereby controlling the amplifier gain so that the mean level of the amplified noise signal is maintained substantially constant.

In this way the noise signal level in each channel can be maintained substantially constant without continual checking and adjustment of the system and this optimises the recognition of fault pulses as the signal is amplified to a maximum extent without the background noise signal being amplified to an extent to produce spurious fault pulses. The noise signal levels in each channel can be maintained the same as one another, this being particularly useful when all the channels are connected by a maximum signal selection circuit to a common comparator circuit.

The time constant of the feed back to the amplifier in each channel will be a matter of some seconds, for example ten seconds, thereby avoiding any change in the amplifier gain resulting from fault produced pulses.

We have also appreciated that the apparatus could be further improved if automatic compensation could be made for intended discontinuities in the reflectivity of the rod occuring at regular intervals along the rod. Such a situation occurs for example in the case of cigarette rod where printed matter appears on the paper wrapper at intervals corresponding to individual cigarette rod lengths. If the apparatus is sensitive enough to recognise unwanted faults, the change in reflectivity from such printed areas may also produce a fault pulse.

In accordance with a further feature of the invention, the comparator means which is responsive to the signal level in the individual channels compares the signal level with a reference level to determine whether the preset allowable level has been exceeded, and means are provided for raising the reference level and thereby reducing the sensitivity of the apparatus, during repetitive periods in which signals resulting from the passage through the inspection head of repetitive acceptable discontinuities in the reflectivity of the rod would be compared in the comparator means.

By appropriately setting the reduction in sensitivity, and synchronising the operation of the means for changing the reference level with the passage of the rod through the inspection head, reflective discontinuities such as those produced by a printing mark on a cigarette rod wrapper, can be prevented from interfering with the detection of unwanted faults.

The comparator reference level can be controlled by means of a gating pulse from a gating circuit.

If the printed mark or other acceptable repeated discontinuity in reflectivity does not encircle the whole rod but only part of the angular periphery of the rod, it may be necessary to provide at least two comparator circuits, one with a steady reference level to receive signals from channels corresponding to groups of the second fibre optic conductors oriented in the head to see the plain rod surface and the other with the variably controlled reference level to receive signals from one or more other channels connected to groups of the second set of fibre optic conductors which are oriented in the inspection head to see the part of the rod periphery incorporating the acceptable discontinuities in reflectivity.

By means of an appropriate logic circuitry, any fault signal recognised by the comparator means may be stored and subsequently used for operating a rejection mechanism when the part of the rod at which the fault has been sensed reaches a rejection point.

BRIEF DESCRIPTION OF THE DRAWING

One example of an optical inspection apparatus constructed in accordance with the invention and, except for the detailed circuitry in FIG. 3, substantially identical to that described in our earlier Specification, and its use on a continuous cigarette rod making machine, is illustrated in the accompanying drawings, in which;

FIG. 3 is a circuit diagram of the optical inspection apparatus;

FIG. 4 is a diagram showing the operation of the FIG. 3 circuit;

FIG. 5 is a y - guide characteristic related to the optical inspection apparatus; and, FIG. 6 is an axial cross section through a rod passing through the circular head.

DETAILED DESCRIPTION OF THE PREFERRED EMBODIMENT

Figure 1:
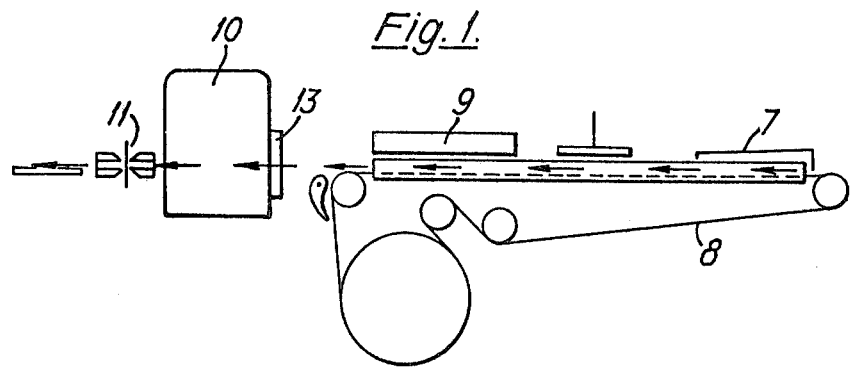
FIG. 1 is a diagrammatic side elevation of the machine.

As shown in FIG. 1 the continuous cigarette rod making machine is conventional in having a garniture 7, through which a garniture tape 8, carries and holds the cigarette paper around the tobacco, the resulting tobacco rod passing beneath a heater 9, through a nucleonic weight control and density monitoring apparatus 10, to a cut off knife 11 which cuts the continuous rod into discrete cigarette lengths. Portions of the rod, corresponding to discrete cigarette lengths, sensed by the nucleonic apparatus 10 as being faulty are rejected and are deflected by a jet of air which is directed at the faulty cigarette immediately after it has been cut from the rod. The apparatus 10 has a memory store which ensures that the deflecting puff of air is provided only when the faulty cigarette has been cut off by the knife 11.

The optical inspection apparatus according to the invention is shown in FIG. 1 at 13 fixed to and immediately upstream of the nucleonic apparatus 10. Any fault in a rod portion as sensed by the apparatus 13 causes a fault signal to be fed into the memory store of the nucleonic apparatus 10 so that again the faulty cigarette is deflected after cutting by the knife 11, the necessary synchronisation being provided by the the circuit of FIG. 3 to be later described.

Figure 2:
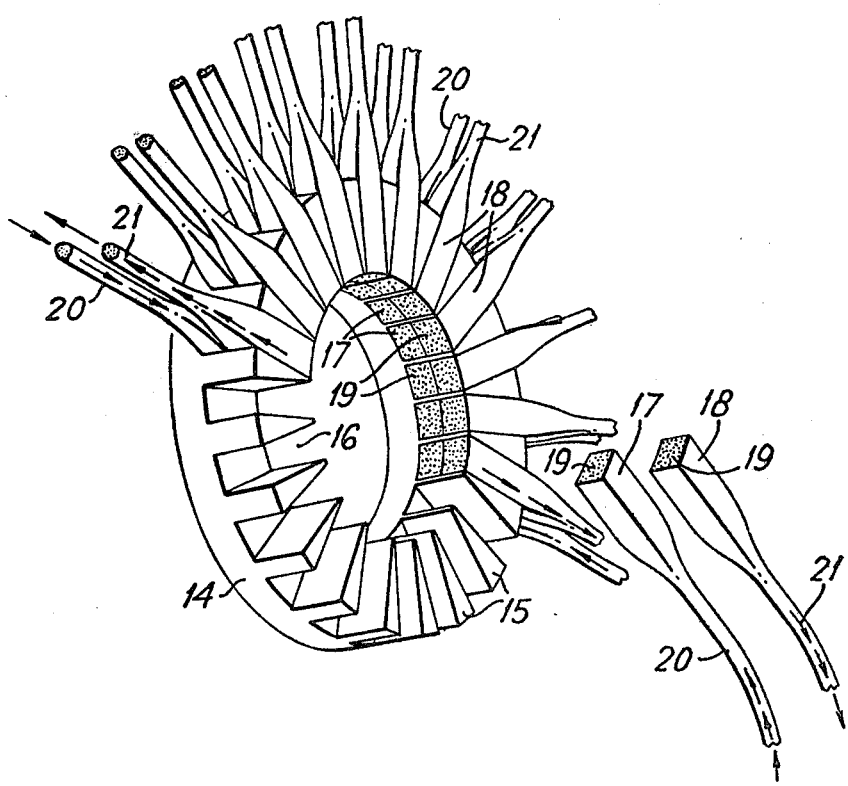
FIG. 2 is a perspective exploded view of the circular head of the optical inspection apparatus.

Physically the optical inspection apparatus 13 has a circular head which is shown in FIG. 2. The head has a support 14 in the form of an annular brass block formed on one face with twenty wedge-shaped radially extending webs 15. Nesting in each slot 16 between adjacent pairs of webs 15 are two layers of blocks 17 and 18 respectively in which are embedded the ends 19 of fibre optic conductor groups forming light guides 20 and 21 respectively. The ends 19 are spread into a rectangular section and are potted in an epoxy resin. The extreme ends of the tips 19 and the end faces of the blocks 17 and 18 are flush with the inner peripheral surface of the block 14, the blocks 17 providing one annular array and the blocks 18 providing a second annular array which is axially spaced from the first array.

As suggested in FIG. 3, light is directed into the other ends of the light guides 20 from a lamp 22. The light is conducted along the guides 20 and is transmitted radially into the head from the first array onto the surface of a cigarette rod passing axially through the head. Light reflected from the surface of the rod is picked up by the ends of the guides in the second annular array and transmitted away to a remote position.

As indicated in FIG. 3, each pair of guides 21 which lead from diametrically opposite positions in the head are united into a common fibre optic guide and the light transmitted along those guides is transmitted from the end of the combined guide onto a separate photo transistor 23 in which the light level is converted into an electrical signal level. The resulting electrical signal is transmitted through an AC coupling capacitor 24, which eliminates the DC component, to a separate amplifier 26 with variable gain adjustment. The amplifier input is the AC voltage developed across a load resistor 25 in the emitter circuit of the photo transistor 23.

The lamp 22 is normally energized through a terminal 27 with 5 volts DC but for test purposes a double ganged switch 28 is changed over so that the lamp is energized from an AC source 29. This is necessary as otherwise no signal will be transmitted by the AC coupling capacitor 24 in the absence of fluctuation caused by a rod passing through the head 14.

Only two channels are illustrated in FIG. 3 but it will be apparent that there are ten channels in all each including a separate photo transistor 23 and amplifier 26. The output of all the amplifiers 26 are connected to a comparator circuit incorporating comparators C+ and C— via a conventional maximum signal selection circuit. This latter circuit includes, for each channel, parallel positive and a negative conducting diodes D+ and D— and a negative and a positive supply rails NL and PL to which all the diodes D+ and all the diodes D— are respectively connected via resistors R1 and R2 respectively. Current from one of the amplifiers 26 will flow through the corresponding diode D+ to the negative supply rail NL. The amplifier supplying this current at any instant will be the amplifier whose output is at the most positive potential at that instant. The potential at the input of the comparator C+ will follow the potential of the most positive amplifier output with a small voltage difference caused by the forward voltage drop across the corresponding diode D+. All the other diodes will be non conducting at the instant considered because they will be biased in the non conducting direction.

When a positive pulse appears at the output of any of the amplifiers 26 due to an imperfection on the surface of the rod, it alone, together with the positive noise signal in that channel, is transmitted to the input of the comparator C+. The outputs of the remaining amplifiers 26 do not contribute to any effect at the input of the comparator C+ provided that their output voltages are all less positive than that appearing at the amplifier transmitting the pulse. The comparator C+ therefore compares with a reference voltage the signal level in one channel at any one time and only the noise level in that channel is relevant.

If the pulse is sufficiently positive to exceed a reference voltage supplied by a reference voltage source 110, representing the allowable limit in the reflectivity of the rod, the comparator C+ produces a fixed amplitude fault pulse at the output.

Each amplifier 26 feeds its own of the second set of diodes D— which conduct negatively going pulses to the positive supply rail PL, this second supply rail being connected to the common input of the comparator C—. The actions of the diodes D— and the operation of the comparator C— is identical to that described above for C+ except that all polarities are reversed. Any fixed amplitude positive going fault pulses produced at the outputs of comparators C+ and C— are combined to produce fault signals through a logical OR gate G.

The amplifier 26 in each channel is provided with an automatic gain control dependant upon the signal noise level in that channel. Thus the gain of an amplifier 26 is controlled by the shunting effect of a field effect transistor 101 whose incremental drain source resistance is in turn controlled by the gate source voltage. The controlling voltage is developed by an amplifier 102 which has for its input the rectified and smoothed output signal from the amplifier 26. On the other input of the amplifier 102 is an adjustable DC voltage controlled by a potentiometer 103. A network 104, 105, 106 and 107 produces a filted voltage approximately proportional to the peak-peak noise signal at the output of the amplifier 26.

The amplifier 102 has a gain of about 30, depending upon the setting of 103, and feeds the gate circuit of the FET 101 via a smoothing network 108 and 109. The drain source resistance of 101 can be varied over the range 500 ohms to 10 K.ohms for a change of about 0.3 volts in gate source voltage. The polarity of feed back via amplifier 102 is such that an increase in mean output noise from the channel causes a decrease in the gain of the amplifier 26. The result is that the system gain adjusts itself so that the mean output noise amplitude remains approximately constant at about 4.5 volts peak-peak determined by the setting of 103. Control is maintained over a range of input amplitude from about 50 mV. to 1 V. peak-peak.

Signals transmitted to the comparators C+ and C— are compared against reference voltages supplied by reference voltage sources 110 and 111 respectively. The reference voltages provided by these sources may be varied by means of a gating circuit to reduce the sensitivity of the comparators in synchronism with acceptable variations in reflectivity of the rod passing through the head 14. As also described, if only part of the angular periphery of the rod is provided with discontinuities in reflectivity, only those channels carrying the signals which vary as a result of such discontinuities will be connected to the comparators incorporating variable reference voltage sources. Other channels carrying signals corresponding to other parts of the rods, may be connected in parallel through a separate maximum signal selection circuit to a separate pair of comparators the reference voltage sources of which are invariable.

FIG. 5 illustrates the y-guide characteristics of the reflected light in the head picked up by the light guides 21. The axis A represents the reflected light picked up and the axis B represents the distance d of the rod surface from the inner peripheral surface of the circular head. The portions marked off on the graph represents variations $\Delta$ d in this distance owing to lateral deviations in the rod relatively to the head. These values will be apparent from FIG. 6 which shows a cigarette rod 31 passing through the head 14. At one position a distance d1 is apparent and at the diametrically opposite position a distance d2. Provided that the distance d is in the substantially straight downward sloping portion of the graph in FIG. 5, the sum of the light picked up by the diametrically opposite guides 21 will be substantially constant irrespective of whether d1 and d2 are equal and of the actual diameter of the rod.

The appearance of a fault signal at the gate G sets a first bistable flip-flop B1. The fault signal is transferred to a second bistable flip-flop B2 upon reception of the first subsequent clock pulse P1 through a monostable circuit M1, the clock pulse immediately resetting the first bistable B1 through a second monostable circuit M2. The fault signal is transmitted from the bistable B2 to a third bistable flip-flop B3 upon reception of the next succeeding clock pulse P2 through a third monostable circuit M3.

Immediately afterwards the clock pulse P2 resets the bistable B2 through a fourth monostable circuit M4.

The sequence of operation controlled by the clock pulses P1 and P2 will be apparent from FIG. 4. At the top of FIG. 4 there is indicated diagrammatically the cigarette rod 31 having consecutive rod portions corresponding to cigarettes L1, L2, L3 and L4 passing from right to left successively through the optical inspection apparatus 13 and the nucleonic apparatus 10. The lower part of FIG. 4 represents the various pulse trains to a common time scale.

The separation of the sensing points of the two monitoring apparatus 13 and 10 is indicated as y and the distance x is the distance by which y exceeds one cigarette length. Both the clock pulses P1 and P2 have a period equal to the time it takes for one cigarette length to pass a fixed point. The leading edge of each pulse P1 is displaced from the corresponding pulse P2 by a time corresponding to the distance y.

FIG. 4 is prepared to represent a case in which a fault signal is produced in the length L1 of the rod by the optical inspection apparatus 13. Thus the fault pulse F is generated and immediately sets the bistable B1. At the next pulse P1 the fault is transmitted to the bistable B2 and at the next pulse P2 the fault signal is transmitted to the bistable B3. It will be seen that the triggering pulse produced by the monostable M3 corresponds with the clock pulse P2 and is immediately followed by the resetting pulse produced by the monostable M4. Similarly, the triggering pulse produced by the monostable M1 coincides with the clock pulse P1 and is immediately followed by the resetting pulse produced by the monostable M2.

The pulses produced by the monostable pulse generators M1, M2, M3 and M4 are very short, for example of the order of 1 microsecond, compared with the time interval of a passage of 1 cigarette length which is typically 15 milliseconds or longer.

The effect of the logic circuitry is that the fault signal is delayed in the bistables B1 and B2 whilst the corresponding rod portion in which the fault has been sensed has just completed its passage through the nucleonic apparatus 10. The fault signal is then brought in synchronism with the potential fault signal produced by the nucleonic apparatus 10 so that potential signals can be stored in a memory store of the apparatus 10 whilst the corresponding rod portion passes to and is cut by the knife 11 prior to deflection by the air jet.

We claim:

1. In an optical inspection apparatus for monitoring a continuously moving rod, said apparatus comprising a circular head through which said rod passes, a first set of fibre optic conductors the ends of which terminate at an inner peripheral surface of said head and which transmits light from a source to said head to illuminate said rod passing therethrough, and a second set of fibre optic conductors the ends of which also terminate at said peripheral surface of the head to pick up light reflected from said rod passing through said head and transmit said reflected light to photoelectric elements, wherein said second set of conductors are divided into angularly spaced groups around said head and selected groups lead to separate ones of said photoelectric elements, the improvement wherein the outputs of said photoelectric elements are fed via A.C. coupling means into separate channels, the D.C. components of said outputs being removed so that the electric signal in each of said channels is a fluctuating noise signal corresponding to fluctuations in the reflectivity of the part of said rod viewed by the respective group of said second set of conductors, said channels being connected to comparator means which is responsive to said noise signal levels in individual ones of said channels and which produces a fault signal if said signal level in any one channel is greater than a preset allowable level, each of said channels including an amplifier for amplifying the output from the respective one of said photoelectric elements, and wherein each of said channels includes means for feeding back to said amplifier a signal related to the mean level of said amplified signal in said channel and for controlling the gain of said amplifier so that the mean level of said amplified noise signal is maintained substantially constant.

2. The improvement according to claim 1, wherein the channels are all coupled to a common comparator circuit via a maximum signal selection circuit which incorporates a plurality of parallel diodes, one for each of said channels, the arrangement being such that at any time only the one of said diodes connected to the one of said channels with the highest signal level conducts.

3. The improvement according to claim 1, wherein said comparator means is responsive to said signal level from said channels for comparing said signal level with a reference level to determine whether said preset allowable level has been exceeded, and wherein means are provided for altering said reference level for reducing the sensitivity of said apparatus during repetitive periods in which signals resulting from the passage through said inspection head of repetitive acceptable discontinuities in the reflectivity of said rod would be compared in said comparator means.

4. The improvement according to claim 1 wherein said comparator means includes a plurality of comparators connected to selected ones of said channels and responsive to the signal level therefrom, each of said comparators comparing a signal level with a reference level to determine whether said preset allowable level has been exceeded, and wherein means are provided for altering said reference level to at least a certain selected comparator for reducing the sensitivity of this comparator during repetitive periods in which signals resulting from the passage of repetitively acceptable discontinuities in the reflectivity of said rod past the group of fibre optic conductors coupled to said certain selected comparator would be compared in said certain selected comparator.

5. In an optical inspection apparatus for monitoring a continuously moving rod, said apparatus comprising a circular head through which said rod passes, a first set of fibre optic conductors the ends of which terminate at an inner peripheral surface of said head and which transmits light from a source to said head to illuminate said rod passing therethrough, and a second set of fibre optic conductors the ends of which also terminate at said inner peripheral surface of the head to pick up light reflected from said rod passing through said head and transmit said reflected light to photoelectric elements, the improvement wherein the output of said photoelectric element is fed via A.C. coupling means into a channel, the D.C. component of said output being removed so that the electric signal in said channel is a fluctuating noise signal corresponding to fluctuations in the reflectivity of said rod, said channel being connected to comparator means which is responsive to said noise signal level in said channel and which produces a fault signal if said signal level in said channel is greater than a preset allowable level, said channel including an amplifier for amplifying the output from said photoelectric element and wherein said channel includes means for feeding back to said amplifier a signal related to the mean level of said amplified signal in said channel and for controlling the gain of said amplifier so that the mean level of said amplified noise signal is maintained substantially constant.

6. The improvement according to claim 1 or 5 wherein signals in said channels producing faults signals are of generally defined duration and wherein said feed back means in each of said channels has a time constant such that signals in said channel which produce fault signals do not appreciably alter the substantially constant mean level of said amplified noise signal.

7. The improvement according to claim 6, wherein the said feed back means has a time constant on the order of several of seconds.

8. In an optical inspection apparatus for monitoring a continuously moving rod, said apparatus comprising a circular head through which said rod passes, a first set of fibre optic conductors the ends of which terminate at an inner peripheral surface of said head and which transmits light from a source to said head to illuminate said rod passing therethrough, and a second set of fibre optic conductors the ends of which also terminate at said peripheral surface of the head to pick up light reflected from said rod passing through said head and transmit said reflected light to photoelectric elements, wherein said second set of conductors are divided into angularly spaced groups around said head and selected groups lead to separate ones of said photoelectric elements, the improvement wherein the outputs of said photoelectric elements are fed via A.C. coupling means into separate channels, the D.C. component of said outputs being removed so that the electric signal in each of said channels is a fluctuating noise signal corresponding to fluctuations in the reflectivity of the part of said rod viewed by the respective group of said second set of conductors, said channels being connected to comparator means which is responsive to said noise signal levels in individual ones of said channels and which produces a fault signal if said signal level in any one channel is greater than a preset allowable level, said comparator means comparing said signal level from said channels with a reference level to determine whether said preset allowable level has been exceeded, and wherein means are provided for altering said reference level for reducing the sensitivity of said apparatus during repetitive periods in which signals resulting from the passage through said inspection head of repetitive acceptable discontinuities in the reflectivity of said rod would be compared in said comparator means.

9. In an optical inspection apparatus for monitoring a continuously moving rod, said apparatus comprising a circular head through which said rod passes, a first set of fibre optic conductors the ends of which terminate at an inner peripheral surface of said head and which transmits light from a source to said head to illuminate said rod passing therethrough, and a second set of fibre optic conductors the ends of which also terminate at said peripheral surface of the head to pick up light reflected from said rod passing through said head and transmit said reflected light to photoelectric elements, wherein said second set of conductors are divided into angularly spaced groups around said head and selected groups lead to separate ones of said photoelectric elements, the improvement wherein the outputs of said photoelectric elements are fed via A.C. coupling means into separate channels, the D.C. component of said output being removed so that the electric signal in each of said channels is a fluctuating noise signal corresponding to fluctuations in the reflectivity of the part of said rod viewed by the respective group of said second set of conductors, said channels being connected to comparator means having a plurality of comparators connected to selected ones of said channels and responsive to said noise signal levels in individual ones of the connected channels, said comparators producing a fault signal if said signal level in any one connected channel is greater than a preset allowable level, each of said comparators comparing a signal level with a reference level to determine whether said preset allowable level has been exceeded, and wherein means are provided for altering said reference level to at least a certain selected comparator for reducing the sensitivity of this comparator during repetitive periods in which signals resulting from the passage of repetitively acceptable discontinuities in the reflectivity of said rod past the group of fibre optic conductors coupled to said certain selected comparator would be compared in said certain selected comparator.

* * * * *

Disclaimer 4,208,578.—*Robert W. McLoughlin* and *Colin P. Nuttall*, Bangor, Northern Ireland. OPTICAL INSPECTION APPARATUS. Patent dated June 17, 1980. Discalimer filed Oct. 30, 1981, by the assignee, *Gallaher Ltd.*

Hereby enters this disclaimer to claims 1, 2, 5, 6 and 7 of said patent.
[*Official Gazette Jan. 5, 1982*]